US010636959B2

United States Patent
Luk (10) Patent No.: US 10,636,959 B2
(45) Date of Patent: Apr. 28, 2020

(54) INSITU CORONA POLING OF PIEZOELECTRIC CERAMICS

(71) Applicant: GENERAL ELECTRIC COMPANY, Schenectady, NY (US)

(72) Inventor: Philip Wayne Luk, Phoenix, AZ (US)

(73) Assignee: General Electric Company, Schenectady, NY (US)

( * ) Notice: Subject to any disclaimer, the term of this patent is extended or adjusted under 35 U.S.C. 154(b) by 572 days.

(21) Appl. No.: 15/476,954

(22) Filed: Mar. 31, 2017

(65) Prior Publication Data

US 2018/0287049 A1    Oct. 4, 2018

(51) Int. Cl.
| | |
|---|---|
| *H01L 41/25* | (2013.01) |
| *H04R 17/10* | (2006.01) |
| *B06B 1/06* | (2006.01) |
| *A61B 8/00* | (2006.01) |
| *H01L 41/257* | (2013.01) |

(52) U.S. Cl.
CPC ........... *H01L 41/257* (2013.01); *H04R 17/10* (2013.01); *A61B 8/00* (2013.01); *B06B 1/0622* (2013.01)

(58) Field of Classification Search
CPC ... H01L 41/257; H01L 41/293; H01L 41/297; H01L 41/31; H04R 17/10
USPC ........................... 310/357, 358; 264/435, 436
See application file for complete search history.

(56) References Cited

U.S. PATENT DOCUMENTS

| | | | | |
|---|---|---|---|---|
| 5,702,629 | A * | 12/1997 | Cui | H01L 41/37 252/62.9 R |
| 6,512,562 | B1 * | 1/2003 | Kobayashi | C08J 7/12 349/122 |
| 2009/0294276 | A1 | 12/2009 | Xu et al. | |
| 2013/0256581 | A1 | 10/2013 | Miyoshi et al. | |
| 2016/0167383 | A1 | 6/2016 | Mizukami | |
| 2016/0190431 | A1 | 6/2016 | Zeng et al. | |
| 2017/0310087 | A1 * | 10/2017 | Wang | H01T 19/04 |

OTHER PUBLICATIONS

International Search Report and Written Opinion issued in connection with corresponding PCT Application No. PCT/US2018/024841 dated Jul. 4, 2018, 10 pages.

* cited by examiner

Primary Examiner — Thomas M Dougherty (57) ABSTRACT

The present disclosure relates to methods of manufacture of piezoelectric ceramic transducers useable, for example, in an ultrasound probe, using a poling process. The poling is accomplished without contacting transducer elements and by subjecting the piezoelectric ceramic transducer to a corona discharge. The disclosure further describes a system for poling a transducer comprising at least one piezoelectric ceramic component or transducer assembly, a ground plane comprising an electrical polarity, and a corona source connected to a first power source configured to supply a first voltage to the corona source having an electrical polarity opposite the electrical polarity of the ground plane. The at least one piezoelectric ceramic component or transducer assembly is positioned between the corona source and the ground plane within a chamber.

17 Claims, 5 Drawing Sheets

FIG. 5

INSITU CORONA POLING OF PIEZOELECTRIC CERAMICS

BACKGROUND

The subject matter disclosed herein relates generally to systems and methods for manufacturing ultrasound transducers, and more particularly to systems and methods for manufacturing and poling piezoelectric ceramic ultrasound transducers.

Ultrasound transducers perform ultrasonic examinations of a subject or sample (e.g., a patient or internal tissues of a patient) during which ultrasonic signals are converted to electrical signals, and vice versa. Ultrasound transducers, all or a portion of which may be housed within a probe, comprise, among other things, acoustic elements which transmit and receive the ultrasound signals. By way of receipt of ultrasound signals, the acoustic elements generate an image of the examined object. The number of acoustic elements in an ultrasound transducer may vary, as may their arrangement (e.g., matrix or linear arrays) and operation (e.g., sequential or phased operation).

At least some known ultrasound transducers utilize piezoelectricity. As is generally known, piezoelectricity is electricity generated by mechanical stress. Piezoelectric transducers comprise a piezoelectric component, in which transduction between mechanical stress and electricity may occur. Certain ceramics, such as lead zirconate titanate (PZT), for example, provide for exemplary piezoelectric components. Resultantly, piezoelectric ceramic transducers are used in a wide range of disciplines which utilize piezoelectric transduction, including medical instrumentation.

During manufacturing of piezoelectric ceramic transducers, piezoelectric ceramic components must be poled prior to use in a transducer. Poling of piezoelectric ceramic components is necessary to align the dipoles within the piezoelectric ceramic component. In a natural state, dipoles within the piezoelectric ceramic component are randomly arranged. Rearranging said dipoles into a polarized orientation is necessary for the piezoelectric component, and thus the transducer, to consistently and effectively transfer electrical and ultrasonic signals. Failure to sufficiently pole the piezoelectric ceramic component results in inferior or unusable ultrasound images, or may prohibit the transducer's use in an ultrasonic imaging device all together.

Piezoelectric ceramic components are commonly poled by manually or physically contacting each acoustic element with an electrode. Contact poling has significant drawbacks, however. For instance, contact poling provides for a relatively high likelihood of inconsistent or ineffectual poling due to manual or machine error in failing to contact each transducer element with the electrode. Some transducers, comprising thousands of acoustic elements and/or large acoustic stacks, make contact poling a highly labor-intensive, laborious process. Moreover, transducers with high numbers of acoustic elements (e.g., 5,000-10,000) require many points of contact by the electrode. As more points of contact are required, the likelihood of failing to contact each element increases, as does the likelihood of damaging the acoustic elements during contact.

Another disadvantage of contact poling is the effect of electrical shorts on the contact-poling process. If an acoustic element is shorted to a ground, for instance, the voltage provided by the poling electrode will not traverse the element to pole the element. Such shorting of one element may also affect other elements, resulting in a multiplication of the number of elements which were not poled.

BRIEF DESCRIPTION

In the present disclosure, systems and methods of non-contact poling are provided, which overcome the above noted deficiencies.

In at least one preferred non-limiting embodiment, a system for poling a transducer is disclosed and described. The system comprises at least one piezoelectric ceramic component or transducer assembly; a ground plane comprising an electrical polarity; and a corona source connected to a first power source. The first power source is configured to supply a first voltage to the corona source having an electrical polarity that is opposite the electrical polarity of the ground plane, and the at least one piezoelectric ceramic component or transducer assembly is positioned between the corona source and the ground plane within a chamber.

In another embodiment, a system for poling a transducer is provided comprising at least one of one or more piezoelectric ceramic transducer assemblies or one or more piezoelectric ceramic components usable in an ultrasound transducer, wherein the one or more piezoelectric ceramic transducer assemblies comprises a non-conductive mask, a piezoelectric ceramic transducer and one or more flexible circuits, the system further comprising a ground plane comprising an electrical polarity, and a corona source, wherein the corona source is connected to a first power source configured to supply a first voltage comprising an electrical polarity to the corona source, wherein the electrical polarity of the first voltage supplied by the first power source is opposite relative to the electric polarity of the ground plane, wherein the at least one of the one or more piezoelectric ceramic transducer assemblies or the one or more piezoelectric ceramic components is positioned between the corona source and the ground plane; and wherein the at least one of the one or more piezoelectric ceramic transducer assemblies or the one or more piezoelectric ceramic components, the ground plane and the corona source reside in a chamber.

In another embodiment, the corona source is suspended above the at least one of the one or more piezoelectric ceramic transducer assemblies or the one or more piezoelectric ceramic components.

In another embodiment, the at least one of the one or more piezoelectric ceramic transducer assemblies or the one or more piezoelectric ceramic components rests upon the ground plane, wherein the electrical polarity of the ground plane is opposite relative to the electrical polarity of the first voltage.

In another embodiment, the system further comprises a conductive grid positioned between the corona source and the at least one of the one or more piezoelectric ceramic transducer assemblies or the one or more piezoelectric ceramic components.

In another embodiment, the conductive grid is connected to the first power source, the first power source being further configured to supply a second voltage comprising an electrical polarity to the conductive grid, wherein the electrical polarity of the second voltage is identical to the electrical polarity of the first voltage.

In another embodiment, the conductive grid is connected to a second power source configured to supply a second voltage comprising an electrical polarity to the conductive grid, wherein the electrical polarity of the second voltage is identical to the electrical polarity of the first voltage.

In another embodiment, the system further comprises an inert gas provided within the chamber.

In another embodiment, the at least one of the one or more piezoelectric ceramic transducer assemblies or the one or more piezoelectric ceramic components is the one or more piezoelectric ceramic transducer assemblies.

In another embodiment, wherein the piezoelectric ceramic transducer comprises a piezoelectric ceramic component and one or more matching layers.

In another embodiment, the piezoelectric ceramic transducer comprises greater than 5,000 acoustic elements.

In another embodiment, the piezoelectric ceramic transducer comprises a lens.

In another embodiment, the inert gas is Argon.

In another embodiment, the ultrasound transducer is a medical ultrasound transducer.

In yet another preferred non-limiting embodiment, a method of manufacturing a piezoelectric ceramic transducer is disclosed and described. The method comprises providing at least one piezoelectric ceramic component or transducer assembly, a chamber, a ground plane in the chamber, and a corona source within the chamber, and positioning the at least one piezoelectric ceramic component or transducer assembly in the chamber between the corona source and the ground plane. The method further comprises supplying a first voltage comprising an electrical polarity to the corona source and generating a corona discharge comprising a range, positioning the at least one piezoelectric ceramic component or transducer assembly within the range of the corona discharge, and performing an acoustic test on the at least one piezoelectric ceramic transducer component or assembly.

In another embodiment, a method of manufacturing a piezoelectric ceramic transducer is provided, comprising: manufacturing at least one of one or more piezoelectric ceramic transducer assemblies or one or more piezoelectric ceramic components, wherein the one or more piezoelectric ceramic transducer assemblies comprise a non-conductive mask and a piezoelectric ceramic transducer, providing a chamber, providing a ground plane in the chamber; providing a corona source within the chamber, positioning the at least one of the one or more piezoelectric ceramic transducer assemblies or the one or more piezoelectric ceramic components in the chamber between the corona source and the ground plane, supplying a first voltage comprising an electrical polarity to the corona source and generating a corona discharge comprising a range, positioning the at least one of the one or more piezoelectric ceramic transducer assemblies or the one or more piezoelectric ceramic components within the range of the corona discharge, and subjecting the at least one of the one or more piezoelectric ceramic transducer assemblies or the one or more piezoelectric ceramic components to acoustic test.

In another embodiment, the method further comprises providing a conductive grid and positioning the conductive grid between the corona source and the at least one of the one or more piezoelectric ceramic transducer assemblies or the one or more piezoelectric ceramic components.

In another embodiment, the method further comprises supplying a second voltage comprising an electrical polarity to the conductive grid, wherein the electrical polarity of the first voltage is identical to the electrical polarity of the second voltage.

In another embodiment, the method further comprises providing an inert gas within the chamber.

In another embodiment, the at least one of the one or more piezoelectric ceramic transducer assemblies or the one or more piezoelectric ceramic components is the one or more piezoelectric ceramic transducer assemblies.

In another embodiment, the method further comprises lensing the piezoelectric ceramic transducer prior to positioning the piezoelectric ceramic transducer within range of the corona discharge.

DETAILED DESCRIPTION

The specifications, composition, structure, size and dimensions of an ultrasound transducer may vary in many respects, such as the quantity and arrangement of acoustic elements. Additionally, as noted herein, the composition, structure, size and dimensions of the components of the presently disclosed systems and methods may also vary. The specifications of the transducer and components of the present disclosure may vary immensely based on the transducer's intended use, for instance. In one embodiment disclosed herein, a piezoelectric ultrasound transducer is described wherein the piezoelectric ultrasound transducer is useable for medical ultrasound imaging, but other transducers for other intended uses, or transducers of differing composition, may be provided. Moreover, the composition of the components of the transducer or the system may be those currently known or later developed.

As used herein, the term "comprising" in the claims and/or the specification is not intended to exclude any additional subject-matter, such as an additional component, step or procedure, whether described herein or not.

Figure 1:
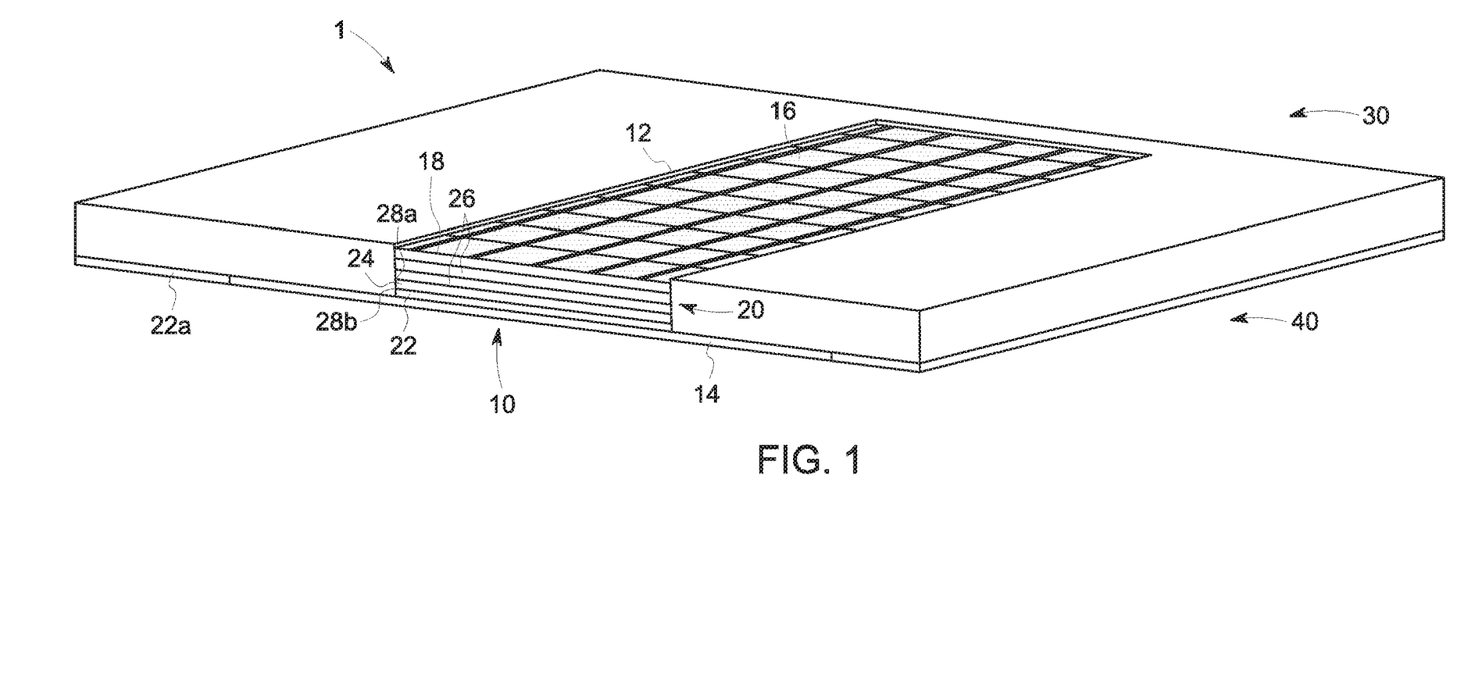
FIG. 1 is a cut-out, cross-sectional view of an ultrasound transducer.

Referring now to the figures, FIG. 1 shows, by way of illustrative and non-limiting example, a transducer assembly (1). The transducer assembly (1) comprises a transducer (10) usable in an ultrasound probe (not shown). The transducer (10) comprises an acoustic stack (20) and a flexible "flex" circuit (14). The transducer assembly (1) further comprises a non-conductive mask (12). Though there exists other suitable structures and orientations of the components of the transducer assembly (1) and/or the transducer (10), the transducer assembly (1) and the transducer (10) of FIG. 1 are illustrative of one structure and orientation suitable for the manufacturing systems and methods described herein.

The transducer (10) is to be poled using the systems and methods described below. More specifically, a piezoelectric ceramic component (24) of the transducer (10) is to be poled. The transducer (10) has a forward-end (30) and a rearward-end (40). A sample (not shown) is ultimately contacted by the transducer (10) toward the forward-end (30) of the transducer (10) when the transducer (10) is used in an ultrasound probe, for instance.

The acoustic stack (20) comprises a de-matching layer (22), the piezoelectric component (24), one or more matching layers (26), and metal layers (28a and 28b). The de-matching layer (22) is formed upon the piezoelectric ceramic component (24). The de-matching layer (22) assists in attenuating ultrasound waves that exit the piezoelectric component (24) in a direction opposite the sample, as well as directs ultrasound waves toward the sample to achieve higher quality imaging. The de-matching layer (22) is provided toward the rearward-end (40) of the transducer (10) relative to the piezoelectric component (24). The de-matching layer may be comprised of any suitable material, such as tungsten carbide, for example.

The piezoelectric component (24) provides a means for piezoelectric transduction and is comprised of any suitable piezoelectric ceramic material, such as PZT, magnesium niobate (PMN) or lead magnesium niobate-lead titanate (PMN-PT). Various processes for manufacturing piezoelectric ceramic components are known in the art. In general, piezoelectric ceramic powders are mixed with additives, tape casted, and laminated to create a monolithic ceramic sheet or ceramic component. The ceramic component sheet or component may be diced (cut) to meet structure- and orientation-related requirements. The diced component is eventually utilized as the piezoelectric ceramic component in a piezoelectric ceramic transducer. The size dimensions of the piezoelectric ceramic component (24) may vary depending on the composition of the piezoelectric ceramic component (24), the intended use of the transducer (10), and other considerations. By way of non-limiting example, the thickness of the piezoelectric ceramic component (24) is between 70 um and 170 um, preferably between 100 um and 120 um.

One or more matching layers (26) of the transducer (10) are also formed on or near the piezoelectric component (24). The one or more matching layers (26) are designed to reduce the difference in impedance between the piezoelectric ceramic (24) and the sample. The one or more matching layers may be of any suitable composition. Known matching layers include acrylonitrile butadiene styrene (ABS), Rexolite, impregnated graphite, or other suitable polymers, for example. The one or more matching layers (26) are provided towards the forward-end (30) of the transducer (10) relative to the piezoelectric component (24). In manufacturing an acoustic stack (20) usable in an ultrasound probe, the stack components are bonded together by any suitable means, such as lamination, for example.

Metal layers (28a and 28b) are indicated on the top side and bottom side of the piezoelectric ceramic component (24) and are provided there along. The metal layers (28a and 28b) serve as electrodes which generate the electrical signals in response to acoustic waves. The metal layers (28a and 28b) may be comprised of any suitable conductive material, such as silver, copper, nickel and/or gold. Metal layer (28a) comprises the ground electrode of the transducer (10).

The size, structure and composition of the de-matching layer (22) and the one or more matching layers (26) may vary depending on the size, structure and composition of the piezoelectric ceramic component (24) or other variables or needs. Those skilled in the art will adjust any and all components of the acoustic stack (20) to comply with desired specifications and the transducer's intended use. As stated, the piezoelectric ceramic component (24) may have a thickness of 70 um and 170 um. The other components in the acoustic stack (20) may, in one non-limiting example, comprise a thickness of 70 um to 170 um, for instance, resulting in a transducer width of approximately 500 um or less, total.

The transducer (10) may further comprise a flexible ("flex") circuit (14) bonded to the piezoelectric ceramic component (24) nearer to the forward-end (30) of the transducer (10) relative to the piezoelectric ceramic component (24). The flex circuit (14) may be of any suitable type and/or composition, such as gold-plated copper traces imbedded in Kapton, for example. Any suitable means may be used to bond the flexible circuit (14) to the piezoelectric ceramic component (24).

The transducer (10) further comprises a backing material (22a) which secures the other transducer (10) components in place and may fill space within the probe in an area between the acoustic stack (20) and the rearward-end (40) of the probe, including the area around the flex circuit (14). Like the de-matching layer (22), the backing material (22a) also prevents ultrasound waves from exiting the piezoelectric component (24) in a direction opposite the sample, as well as directs ultrasound waves towards the sample. In this way, in some embodiments the backing material (22a) may replace the de-matching layer (22). The backing material (22a) may be comprised of any suitable material, such as a metal- or ceramic-filled epoxy, graphite, or aluminum, for example.

The transducer assembly (1) further comprises the non-conductive mask (12). As described in further detail below, the non-conductive mask (12) provides a barrier to the passage of charged ions during the poling processes described herein. The acoustic stack (20) is partially enveloped by the non-conductive mask (12) in the transducer assembly (1). Gaps (16) may exist in the non-conductive mask (12) to facilitate the poling of the piezoelectric ceramic component (24). The non-conductive mask (12) may be comprised of any suitable non-conductive material, such as Teflon.

In some known piezoelectric manufacturing processes, lensing of the transducer (10) may occur by which a final matching layer—a lens (18)—may optionally be formed upon the transducer (10) furthest from the piezoelectric ceramic component (24) toward the forward-end (30) of the transducer (10). The lens (18) serves as a water- and/or air-tight seal for the transducer (10) components. The structure of the lens (18) may vary depending on various factors, such as the intended use of the lens (18) and/or the transducer. For example, the lens (18) may be flat or possess one or more curves, and be of any other size, shape or dimensions to meet required transducer specifications. Adding a lens (18) may increase the width of the transducer (10). A lensed transducer, however, may still have a width of less than 1 mm.

Because the lens (18) is the object and/or layer which contacts the sample, the composition of the lens (18) is subject to biological considerations in addition to mechanical and acoustic considerations. The specifications and/or composition of the lens (18) is thus dependent upon mechanical, acoustic, and biological needs, among others. A typical lens (18) may be comprised of, for instance, room temperature vulcanization (RTV) silicone, urethane or other low density polymers.

The process of applying a lens (18) generally comprises manufacturing a lens (18) and bonding the lens (18) to the piezoelectric ceramic transducer (10). By way on one non-limiting example, the lens (18) may be manufactured by casting, and the lens (18) may be bonded by any suitable means, such as lamination.

Considering the drawbacks of contact-poling described above, systems and methods non-contact poling are further provided. As disclosed herein, subjecting piezoelectric ceramic components and/or transducers to corona discharge provides a method by which acoustic elements, particularly large quantities of acoustic elements, may be poled without physical contact to each acoustic element by an electrode.

In poling the piezoelectric component of a piezoelectric transducer using corona discharge, a chamber is provided, and a transducer assembly (e.g., transducer assembly (1)), a high voltage ground plane, and a corona source, such as a corona needle, are positioned within the chamber. The transducer assembly comprises a transducer and may comprise a non-conductive mask, such as the transducer and mask described above. The transducer is positioned between the corona source and the high voltage ground plane. The corona source is connected to a power source which supplies electricity to the corona source. When sufficiently high voltages are supplied to the corona source, corona discharge occurs at or near the corona source whereby a fluid surrounding the corona source, such as air, is ionized; charged ions emanate from near the corona needle and comprise the corona discharge.

The charged ions attract toward an oppositely-charged ground plane, encountering the transducer assembly in route towards the ground plane. The ions, upon reaching the non-conductive mask, begin to build up on one side of the transducer assembly. The buildup of charge on the one side of the transducer assembly ultimately results in an equilibrium between the charged side of the transducer and the high voltage ground plane such that an electrical field exists across the transducer and thus across the piezoelectric ceramic component. Thereby, the piezoelectric ceramic component is poled.

Notably, corona poling provides significant advantages over contact poling. For instance, corona poling may be carried out in easily accessible and reproducible environments, such as room temperature, air environments. Corona poling also negates concerns regarding electrical shorting, for even if an element in a transducer subject to corona-poling is shorted to ground, the electrical field generated between the surface of the transducer assembly and the ground plane will still traverse the acoustic element and successfully pole the element.

Figure 2:
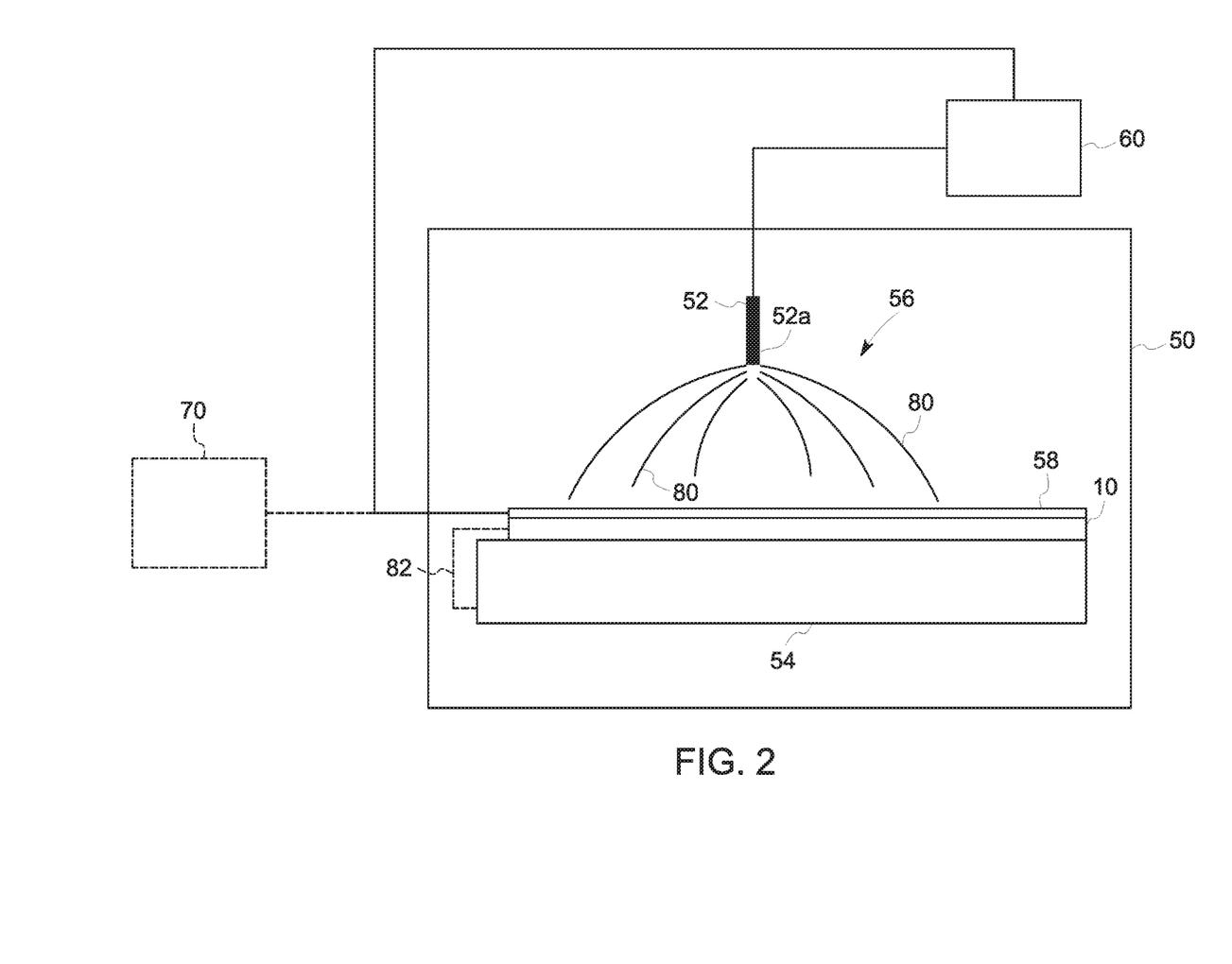
FIG. 2 is a schematic diagram of a system for poling an ultrasound transducer described herein.

FIG. 2 illustrates a system for poling a piezoelectric ceramic transducer assembly using corona discharge. The system comprises a transducer assembly (1) (a simplified illustration of the transducer assembly (1) of FIG. 1) comprising a piezoelectric ceramic transducer (10). The system further comprises a chamber (50), a corona source (52), a first power source (60), and a high voltage ground plane (54). The piezoelectric ceramic transducer assembly (1) and the high voltage ground plane (54) reside within the chamber (50). The high voltage ground plane (54) may be comprised of any suitable composition, such as copper. The piezoelectric ceramic transducer assembly (1) resides within the chamber (50) and may rest upon on a high voltage ground plane (54).

Notably, the presently disclosed system may be used to pole one or more piezoelectric ceramic transducer components (24) or one or more piezoelectric ceramic transducer (10) wherein the one or more piezoelectric ceramic components (24) are already assembled in the one or more transducers, or one or more lensed piezoelectric ceramic transducers. More specifically, one or more piezoelectric ceramic components may be poled (i) while still in the form of a monolithic ceramic sheet prior to dicing; (ii) after dicing, but prior to the piezoelectric ceramic component's assembly into a transducer; (iii) after assembly into a piezoelectric ceramic transducer; or (iv) after lensing the piezoelectric ceramic transducer. For purposes of the present description, poling of one or more piezoelectric ceramic components wherein the one or more piezoelectric ceramic components (24) are already assembled in the one or more transducers is provided.

The chamber (50) may be of any suitable composition, such as a plexiglass, vacuum chamber. The chamber (50) may also comprise means for introducing a gas into the chamber as well as path-through for connections to various system components which may reside outside of the chamber (50), such as one or more power sources (60, 70). The size of the chamber (50) may also vary, but must be large enough to house a corona source (52) and one or more piezoelectric transducer components, one or more piezoelectric ceramic transducers, and/or one or more piezoelectric ceramic transducer assemblies. A fixturing (82) of any suitable type and/or composition may optionally be provided to connect the transducer ground plane (28b) to the high voltage ground plane (54).

The corona source (52) (e.g., a corona needle) resides within the chamber (50) and is suspended above the piezoelectric ceramic transducer assembly (1). Though the corona source (52) is shown as being suspended above the piezoelectric ceramic transducer assembly (1), any suitable arrangement may be used, so long as the corona source (52) is positioned opposite to the high voltage ground plane (54). For instance, the corona source (52) may be below the piezoelectric ceramic transducer assembly (1) and the high voltage ground plane (54) or to one side or the other of the piezoelectric ceramic transducer assembly (1) and the high voltage ground plane (54).

The first power source (60) is connected to the corona source (52) by any suitable means which are configured to supply a voltage from the first power source (60) to the corona source (52). The first power source (60) may reside inside or outside the chamber (50). The first power source (60) is configured to provide sufficient voltage to the corona source (52) to create a corona discharge (56). The first power source (60) is configured to provide any necessary voltage, but is preferably configured to provide a voltage to the corona source (52) between 8-20 kilovolts, most preferably 10 kilovolts. The first power source (60) is further configured to provide constant or variable voltage, or both. The electrical polarity of the voltage supplied to the corona source (52) may be positive or negative.

As further demonstrated in FIG. 2, a conductive grid (58) comprising any suitable grid spacing, such as approximately 500 um, for example, may be positioned between the piezoelectric ceramic transducer (10) and the corona source (52). The conductive grid (58) acts as a collimator to funnel charged particles (80) (ions) from a position near the corona source towards the ground plane, and thus towards the transducer, which is positioned between the corona source and the ground plane. The conductive grid (58) may be comprised of any suitable conductive material, such as copper, molybdenum, stainless steel, or alloys thereof. Preferably, the conductive grid (58) is comprised of stainless steel.

The conductive grid (58) may be connected to the first power source (60) or a second power source (70). The power source which supplies the voltage to the conductive grid (58) may reside inside or outside of the chamber. The power source which supplies voltage to the conductive grid (58) supplies a second voltage to the conductive grid (58). Said power source is configured to provide any suitable voltage to the conductive grid (58), and is preferably configured to provide a voltage in the range of 2-3 kilovolts. Notably, the voltage supplied to the conductive grid (58) should not exceed 5 kilovolts as this creates a parasitic corona.

The power source which supplies the second voltage to the conductive grid (58) is connected to the conductive grid (58) by any suitable means configured to supply the second voltage. The power source which supplies the second voltage to the conductive grid (58) is further configured to provide constant or variable voltage, or both, and is further configured to supply a constant current. The electrical polarity of the second voltage supplied to the conductive grid (58) may be positive or negative, but must be identical to the electrical polarity of the first voltage and opposite relative to the electrical polarity of the high voltage ground plane (54).

As described above and further demonstrated in FIG. 2, sufficient voltage is supplied by the first power source (60) to the corona source (52), whereupon the voltage emanates from near the corona source tip (52a), causing a discharge of voltage, which ionizes gas and/or fluid particles (80) surrounding the corona source (52). In other words, charged ions (80) (plasma) result when voltage discharges near the corona source (52); the charged ions (80) comprise a corona discharge (56).

The desired distance between the tip (52a) of the corona source (52) and the piezoelectric ceramic transducer assembly (1) is dependent upon the strength of voltage supplied to the corona source (52), the range of the resultant corona discharge (56), the size of the piezoelectric ceramic component (24), and the size of the piezoelectric ceramic transducer (10), among other considerations. The charged ions (80) must be near enough to the conductive grid (58) and the high voltage ground plane (54) to be attracted in the direction of the transducer assembly (1) and move in the direction of the transducer assembly (1) and the ground plane (54). Preferably, the distance between the corona source tip (52a) and the transducer assembly (10) is 10 mm to 100 mm, most preferably 50 mm.

The charged ions (80) emanating from near the corona source possess an electrical polarity (i.e., a positive or negative charge) which is identical to that of the conductive grid (58) but opposite to that of the ground plane (54). The electrical polarity of the ions (80) is dependent on the electrical polarity of the voltage provided by the power source (60). Thus, the corona source (52) may receive and harbor voltages of positive or negative electrical polarity, leading to the creation of positively- or negatively-charged ions.

As will be clear to those in the art, the electrical polarity of a corona source (52), which is determined by the electrical polarity of the voltage supplied to said corona source (52), must be identical to that of the conductive grid (58) and opposite to that of the high voltage ground plane (54). Such opposition of electrical polarity between the corona-poling system's components facilitates polarization of the piezoelectric ceramic component (54). By way of one example in FIG. 3, a first voltage with positive polarity is supplied to the corona source (52) by the first power supply (60). A second voltage with positive electrical polarity is supplied to the conductive grid (58), wherein the second voltage is supplied by a second power source (70). The high voltage ground plane (54), in contrast, possesses negative polarity.

Figure 3:
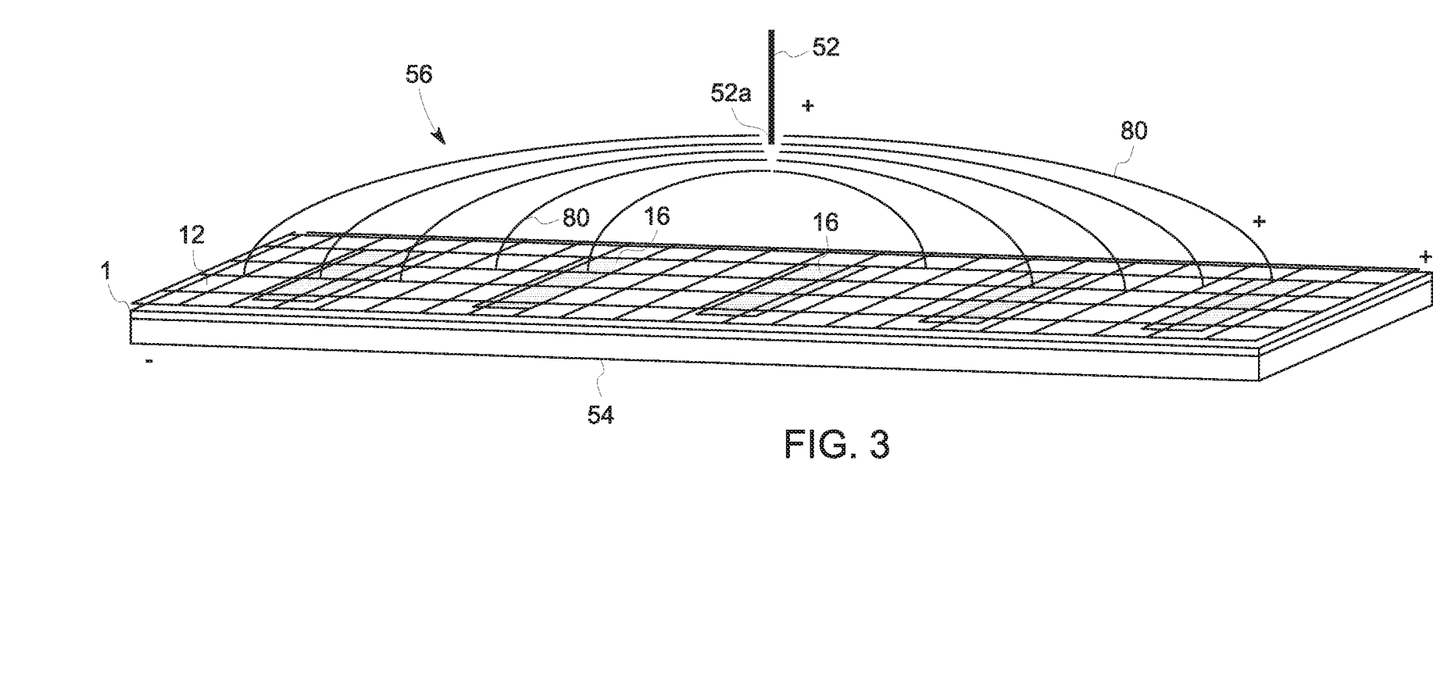
FIG. 3 is a cross-sectional view of a system for poling an ultrasound transducer described herein.

In the system of FIG. 3, the transducer assembly (1), the corona source, the conductive grid (58) and a high voltage ground (54) are shown. The non-conductive mask (12) of the transducer assembly (1) may provide for gaps (16) whereby a transducer and or a lens (18) of a transducer may be exposed to the charged ions (80). The exposure provided by the gaps (16) facilitates attraction between the ions (80) and the ground plane (54).

As corona discharge (56) occurs, the particles (80) are ionized and obtain a positive charge. The opposing electrical polarity of the ions (80) relative to the ground plane (54) results in an electrical attraction between the ions (80) and the ground plane (54). The conductive grid (58), possessing identical electrical polarity as the ions (80), acts as a collimator to funnel the charged ions (80) to desired locations on the transducer assembly (1).

Because the electrical polarity of the conductive grid (58) is the same as the ions (80), the conductive grid (58) will repel the ions (80). But the repellant strength of the conductive grid (58) is not enough to push the ions (80) away, which results in a funneling effect of the ions (80) by the conductive grid (58). Funneling of the charged ions (80) leads to an accumulation of charged ions (80) at or near the surface of the transducer assembly (1). Buildup of ions (80) occurs thereupon because of the relative quantity of non-conductive material covering the ground plane (54) such that the only path for the charge to dissipate is slowly through any leak points.

As the charged ions (80) accumulate on the surface of the transducer assembly (1), the charge of the ions (80) is transferred (or shed) to the transducer assembly (1) and the ions (80) are neutralized. The positively-charged surface of the transducer assembly (1) creates an electrical equilibrium with the negatively-charged ground plane (54), whereby an electrical field is created across the transducer assembly (1). The dipoles within the piezoelectric ceramic component (24) thereby become aligned to achieve the polarity necessary for piezoelectric transduction.

The ionized gas and/or fluid particles (80) surrounding the corona source (52), or any other suitable particles. Preferably, the ionized gas and/or fluid particles (80) are of an inert gas, such as Argon, or any other suitable inert gas. Though air/oxygen environments are suitable for the corona poling process described herein, inert gases are preferred because other fluids or gases, such as oxygen, are more reactive than inert gases. Higher degrees of reactiveness of the ionized particles may result in damage to transducer components.

Figure 4:
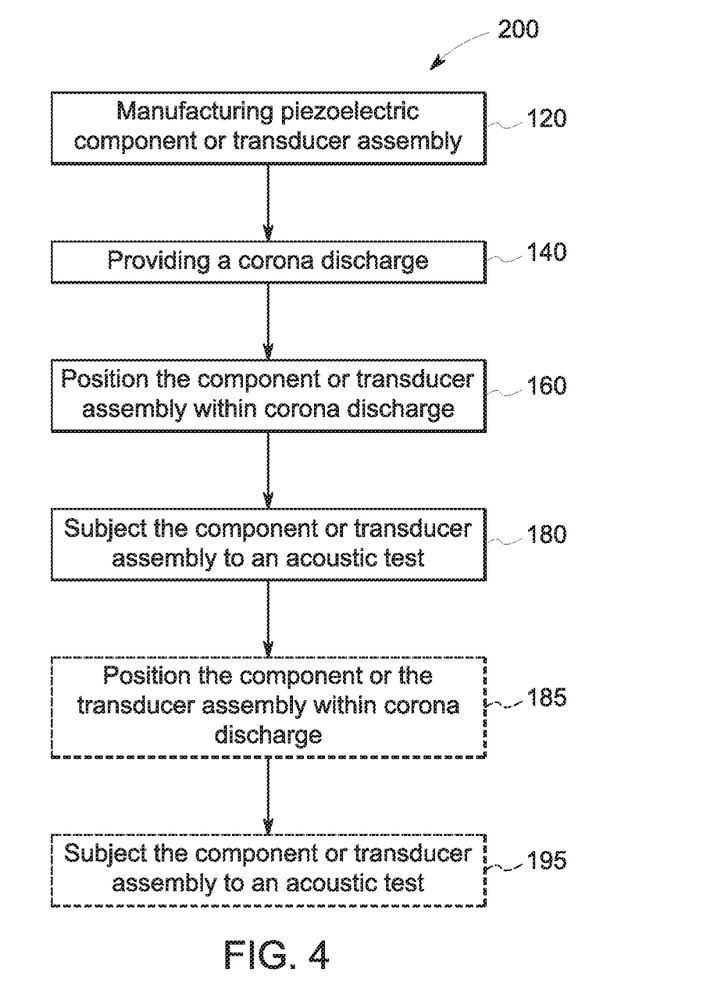
FIG. 4 is a schematic diagram of a method for manufacturing an ultrasound transducer described herein.

FIG. 4 illustrates a method (100) in which the piezoelectric ceramic component (24) is poled. As described above, the piezoelectric ceramic component (24) may be in varying steps of the transducer manufacturing process when the component is poled. And, notably, the methods of both FIG. 4 and FIG. 5 may be carried out upon one or more piezoelectric ceramic components, one or more piezoelectric transducer assemblies comprising a piezoelectric ceramic transducer, or both.

In step 120, one or more transducer assemblies comprising a piezoelectric ceramic transducer are manufactured. In step 140, a corona discharge is provided. In step 160, the one or more transducer assemblies are positioned within a range of the corona discharge to pole the ceramic component of the piezoelectric transducer. And finally, in step 180, the one or more piezoelectric ceramic transducer assemblies (1) are subjected to a first acoustic test to ensure proper polarization was achieved.

Regarding the first acoustic test performed to ensure proper polarization of the piezoelectric ceramic transducers, any suitable method may be used, such as basic in-tank acoustic testing or image quality analysis. If the polarization of the piezoelectric component is insufficient, the poling process and acoustic test may be repeated, as shown in optional steps 185 and 195, respectively, until desired polarity is achieved.

Figure 5:
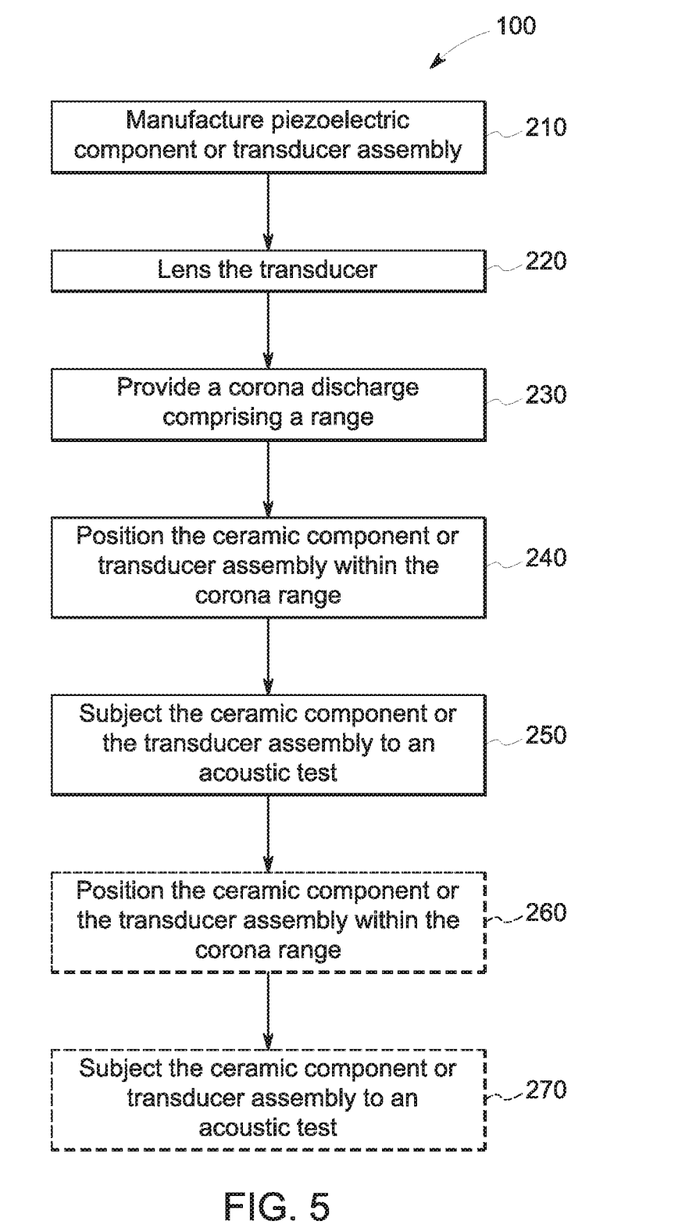
FIG. 5 is a schematic diagram of another method for manufacturing an ultrasound transducer described herein.

FIG. 5, illustrates another method (200) in which the piezoelectric ceramic component is poled. In step 210 one or more transducer assemblies comprising a piezoelectric ceramic transducer are manufactured. In step 220, a lens is provided to each of the piezoelectric transducers. The lens may be manufactured by any suitable method, such as casting, and may be composed of any suitable material, as described above.

In step 230, a corona discharge is provided. In step 240, the one or more transducer assemblies comprising a lensed piezoelectric transducer are positioned within range of the corona discharge to pole the piezoelectric ceramic component of the lensed piezoelectric ceramic transducer.

It should be noted that poling may be completed before lensing or after lensing, or both before and after lensing. Similarly, acoustic tests may occur, for example: (i) after poling but before lensing; (ii) after lensing; or (ii) before and after lensing.

In step 250, the one or more lensed piezoelectric transducers are subjected to a first acoustic test to ensure proper polarization was achieved. And again, if the polarization of the piezoelectric component is insufficient, the poling process and acoustic test may be repeated, as shown in optional steps 260 and 270, respectively, until desired polarity is achieved.

Though poling the piezoelectric ceramic transducer before lensing is a suitable method for manufacturing the transducer, drawbacks of this approach exist. For instance, if a transducer was poled, then tested and then lensed, optimum polarization would not survive the lensing because the ceramic is heated during the lensing process. Heating reduces the polarization of the ceramic and, at certain temperatures (a temperature above the ceramic's Curie temperature, for instance), the heat can completely negate the ceramic's polarization. Poling processes whereby the transducer is poled after lensing may therefore be desirable.

Poling of different piezoelectric ceramic components via the corona-poling methods of FIGS. 4 and 5 may require different lengths of time to achieve proper polarization of the piezoelectric ceramic component. Typical ceramics used in ultrasound transducers, such as PZT, may require between up to 15 minutes within the corona discharge. Generally, poling should last at least 5 minutes to provide an adequate opportunity for the ceramic to be poled.

It must be noted that though the systems and method described herein may be utilized in poling a single transducer or a single piezoelectric ceramic component usable in a transducer, the systems and methods described herein may also be utilized in poling multiple ultrasound transducers or multiple piezoelectric ceramic components simultaneously. Similarly, multiple corona sources, conductive grids and/or ground planes may be used to conduct the corona poling. And, as previously stated, the piezoelectric ceramic component may be in various forms, such as a monolithic sheet, a post-diced form, and/or assembled into a transducer.

In certain embodiments, the piezoelectric ceramic transducer assembly or piezoelectric ceramic component does not rest upon a high voltage ground plane. The piezoelectric ceramic transducer assembly, for instance, may rest within the chamber on any other suitable platform, or be suspended or positioned using any suitable means, so long as the platform or other means do not interrupt the electrical field generated between the high voltage ground plane and the surface of the transducer assembly. The piezoelectric ceramic transducer assembly must, however, reside between the high voltage ground plane and the corona source and be near enough to the high voltage ground plane and the corona source so that the electrical field generated between the high voltage ground plane and the surface of the transducer assembly poles the piezoelectric ceramic component.

The written description uses embodiments/examples to disclose the invention, including the best mode, and also to enable any person skilled in the art to practice the invention, including making and using any devices or systems and performing any incorporated methods. The patentable scope of the invention is defined by the claims, and may include other embodiments/examples that occur to those skilled in the art. Such other embodiments/examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of said elements or steps, unless such exclusion is explicitly stated. Furthermore, references to "one embodiment" or "another embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for poling a transducer comprising:
    a transducer assembly having at least one piezoelectric ceramic component;
    a ground plane comprising an electrical polarity;
    a corona source connected to a first power source configured to supply a first voltage to the corona source having an electrical polarity opposite the electrical polarity of the ground plane;
    a conductive grid positioned between the corona source and the transducer assembly; and
    a fixturing to connect a transducer ground plane of the transducer assembly with the said ground plane;
    wherein the transducer assembly is positioned between the corona source and the ground plane within a chamber.

2. The system of claim 1, wherein the corona source is suspended above the transducer assembly.

3. The system of claim 2, wherein the transducer assembly rests upon the ground plane, wherein the electrical polarity of the ground plane is opposite the electrical polarity of the first voltage.

4. The system of claim 1, wherein the conductive grid is connected to the first power source, the first power source being further configured to supply a second voltage comprising an electrical polarity to the conductive grid, and the electrical polarity of the second voltage is identical to the electrical polarity of the first voltage.

5. The system of claim 1, wherein the conductive grid is connected to a second power source configured to supply a second voltage comprising an electrical polarity to the conductive grid, and the electrical polarity of the second voltage is identical to the electrical polarity of the first voltage.

6. The system of claim 5, further comprising an inert gas provided within the chamber.

7. The system of claim 6, wherein the transducer assembly is an assembly comprising a non-conductive mask, a piezoelectric ceramic transducer and one or more flexible circuits.

8. The system of claim 7, wherein the piezoelectric ceramic transducer comprises one or more matching layers.

9. The system of claim 7, wherein the piezoelectric ceramic transducer comprises greater than 5,000 acoustic elements.

10. The system of claim 8, wherein the piezoelectric ceramic transducer comprises a lens.

11. The system of claim 10, wherein the inert gas is Argon.

12. The system of claim 11, wherein the piezoelectric ceramic transducer is an ultrasound transducer.

13. A method of manufacturing a piezoelectric ceramic transducer comprising:
   providing a transducer assembly having at least one piezoelectric ceramic component;
   providing a chamber;
   providing a ground plane in the chamber;
   providing a corona source within the chamber;
   positioning the transducer assembly in the chamber between the corona source and the ground plane;
   providing a conductive grid and positioning the conductive grid between the corona source and the transducer assembly;
   providing a fixturing to connect a transducer ground plane of the transducer assembly with the said ground plane;
   supplying a first voltage having an electrical polarity to the corona source and generating a corona discharge comprising a range;
   positioning the transducer assembly within the range of the corona discharge; and
   performing an acoustic test on the transducer assembly.

14. The method of claim 13, further comprising supplying a second voltage comprising an electrical polarity to the conductive grid, wherein the electrical polarity of the first voltage is identical to the electrical polarity of the second voltage.

15. The method of claim 14, further comprising providing an inert gas within the chamber.

16. The method of claim 15, wherein the transducer assembly is an assembly comprising a non-conductive mask, a piezoelectric ceramic transducer and one or more flexible circuits.

17. The method of claim 14, further comprising lensing the piezoelectric ceramic transducer prior to positioning the piezoelectric ceramic transducer within range of the corona discharge.

* * * * *